United States Patent [19]

Murata et al.

[11] 4,443,355

[45] Apr. 17, 1984

[54] DETERGENT COMPOSITION

[75] Inventors: Moriyasu Murata, Chiba; Akira Suzuki, Funabashi; Atsuo Nakae, Saitama; Susumu Ito, Tochigi, all of Japan

[73] Assignee: Kao Corporation, Tokyo, Japan

[21] Appl. No.: 507,426

[22] Filed: Jun. 23, 1983

[30] Foreign Application Priority Data

Jun. 25, 1982 [JP] Japan .................................. 57-109473

[51] Int. Cl.$^3$ .......................... C11D 3/386; C12N 9/42
[52] U.S. Cl. ....................... 252/174.12; 252/DIG. 12; 435/209; 435/263; 435/264; 435/822
[58] Field of Search .................. 252/174.12, DIG. 12; 435/264, 263, 209, 822

[56] References Cited

FOREIGN PATENT DOCUMENTS 2094826A 9/1982 United Kingdom .
2095275A 9/1982 United Kingdom .

Primary Examiner—John E. Kittle
Assistant Examiner—Mukund J. Shah
Attorney, Agent, or Firm—Flynn, Thiel, Boutell & Tanis

[57] ABSTRACT

A detergent composition contains as an active component a cellulase produced by alkalophilic bacteria of the genus of Cellulosmonas.

2 Claims, No Drawings

DETERGENT COMPOSITION

The present invention relates to a detergent composition. More particularly, the invention relates to a detergent composition characterized by containing a specified cellulase which is produced by specified cellulase-producing bacteria and which exhibits a high enzymatic activity even under alkaline conditions.

Recently, the techniques of deterging clothes have been improved remarkably. More particularly, the deterging of clothes has been facilitated remarkably because of the development of starting materials for detergents, improvement in quality of water, improvement and spread of deterging machines and improvement of the fibers. Particularly, the improvement of the starting materials for detergents are remarkable. Since surfactants, builders, dispersing agents, fluorescent dyes and bleaching agents have been improved, it is considered that compositions of detergents for clothes have reached the completion. The detergents for clothes have been developed on the basis of ideas of (1) reducing interfacial tension between dirts or/and the fiber and water by adsorption of a surfactant and a builder on the surface of the dirts or/and the fiber and, therefore, physicochemically separating the dirts from the fibers, (2) dispersing and solubilizing the dirts with a surfactant or an inorganic builder, (3) chemically decomposing the dirts with an enzyme such as protease, (4) bleaching colored dirts with a bleaching agent or the like, (5) bleaching the surface of fibers by adsorption of a fluorescent dye or the like thereon, (6) preventing precipitation of components effective for the deterging due to divalent metal ions with a chelating agent.

The basic idea of deterging clothes is effective incorporation of components which directly attack the dirts or components which assist the attack as ingredients of the detergent compositions. The intended deterging capacity of the detergent compositions has substantially reached the saturation. Therefore, great efforts are required to further improve the deterging power.

The inventors have found that a cellulase produced by a specified cellulase-producing microorganism has a deterging power far superior to that of conventional cellulase-containing detergents and reduction in activity thereof is only slight even under alkaline conditions. The present invention has been completed on the basis of this finding.

The specified cellulase used in the present invention is produced by alkalophilic bacteria of the genus of Cellulomonas. This cellulase maintains its high activity even under alkaline conditions and it is resistant to alkali.

The microorganism used for the production of the enzyme used in the present invention is any of the alkalophilic bacteria of the genus of Cellulomanas capable of producing the cellulase according to the present invention and varieties thereof.

As an example of strains of the alkalophilic bacteria of the genus of Cellulomonas, there may be mentioned Cellulomonas sp. No. 301-A.

The principal bacteriological properties of Cellulomonas sp. No. 301-A are as follows:
(a) morphology:
1. bacillus ($0.4-0.6\mu \times 1.0-1.2\mu$),
2. having one motile polar flagellum,
3. free of spore formation,
(b) physiological properties:
1. growth pH range: pH 6.0–10.3
2. cell wall-constituting amino acid: ornithine.

In the gas chromatographic analysis of methyl esters of fatty acids contained in the microbial bodies, a large peak of an anteiso-$C_{15}$ fatty acid was detected. From these results, it was confirmed that the bacteria belong to the genus of Cellulomonas. This bacteria was deposited at the Fermentation Research Institure, the Agency of Industrial Science and Technology, located at 1-3, Higashi 1-chome, Yatabe-machi, Tsukuba-gun, Ibaraki-ken 305, Japan on June 17, 1982 under FERM P-6582, which was then transferred to International deposit under Budapest Treaty on June 10, 1983 under FERM BP-305. Accordingly it is available to any person from the above mentioned authority.

Cellulomonas sp. No. 301-A produces a high unit of alkali cellulase and accumulates this enzyme in a culture liquid. As a carbon source in the culture medium, any of known carbon sources such as CMC or Avicel may be used. Ammonium salts, nitric acid salts, organic substances, inorganic metal salts, yeast extract, etc. may be incorporated in the culture medium. The pH of the culture medium is controlled to 7 to 10.3, preferably around 9.5 with sodium carbonate, sodium hydrogencarbonate or the like during the culture.

As the cellulase used in the present invention (hereinafter referred to as alkali cellulase 301-A), there may be mentioned either the culture liquid per se or a crude enzyme solution obtained by removing the microbial bodies from the culture liquid by centrifugation or the like. Further, an enzyme powder obtained by purifying the above-mentioned crude enzyme solution by ammonium sulfate fractionation or precipitation with an organic solvent such as acetone or ethanol may also be used.

Alkali cellulase 301-A used in the present invention liquefies or solubilizes celluloses such as Avicel or CMC. The optimum pH for exhibiting the activity of decomposing Avicel and CMC is 5.5 to 7.5. The stable pH range is 5.2 to 11.0. The enzyme comprises a mixture of at least five enzymes including three exo-type CMC-decomposing enzymes, endo-type CMC-decomposing enzyme and Avicel-decomposing enzyme.

The present invention is characterized in that the specified cellulase is contained as a component of the detergent composition. The present invention provides a detergent composition having a remarkable deterging power for inorganic stains or dirts which cannot be removed generally according to cellulase activity, particularly dirts on a collar comprising a mixture of inorganic dirts and oils and fats secreted on the skin surface which mixture is changing its quality with time.

It has been well known to use enzymes in the technical field of detergents as described above, but known enzymes are only those which act effectively particularly on the dirts. Namely, it has been known to use protease for protein dirts, amylase for starch dirts and lipase for oily dirts. They attack directly the dirts. The deterging mechanism with the cellulase according to the present invention has not completely been elucidated yet. It can be said, however, that the deterging effect is not based on the mere swelling effect on the fibers, unlike surfactants.

A great advantage of the present invention is that the detergent composition is effective for removing not only stains on collar and cuffs and grease stains but also inorganic solid stains such as fine muddy dirts which could not be removed sufficiently by using conventional detergents. Another great advantage of the invention is that the detergent composition is effective also for improving deterging power of phosphorus-free detergents or detergents having only a low phosphorus content. For removing fine muddy dirts got into the fibers, phosphates have been used effectively. However, phosphate contents of the detergents have gradually been reduced recently due to a problem of eutrophication. In addition, under some unavoidable circumstances, phosphate-free detergents are required and, therefore, the removal of the muddy dirts has become difficult. It has been known that the removal of muddy dirts got into a texture of a cotton cloth is difficult particularly when grease dirts are also present. Particularly, muddy dirts on canvas shoes made of blended cotton fiber are great distress to housewives.

The detergents of the present invention cast a fresh light on the above-mentioned subjects. Namely, when the present invention is applied to (1) alkaline detergents free of phosphates or having only a low phosphate content or (2) weakly alkaline, liquid, phosphate-free detergents, a high deterging power equal to or even higher than that of a weakly alkaline, powdery detergent containing a sufficient amount of the phosphate can be obtained in the removal of muddy dirts from cellulose fibers and cellulose blended fibers. The specified cellulases may be incorporated also in a neutral or weakly acidic detergent.

Another great advantage of the present invention is that the present invention may be applied to detergents of any desired form. The detergent compositions of the present invention can be obtained by incorporating the cellulase in compositions in various forms such as spray-dried powder, powder-blended powder, tablets and liquid.

The components other than the cellulase in the detergent composition of the present invention are not particularly limited. For example, the components may be selected from the following components depending on the intended effects.

[1] Surfactants:
(1) straight-chain or branched alkylbenzenesulfonates having alkyl groups having 10 to 16 carbon atoms in average,
(2) alkyl or alkenyl ether sulfates having straight-chain or branched alkyl or alkenyl groups having 10 to 20 carbon atoms in average and also having 0.5 to 8 mol in average of added ethylene oxide, propylene oxide or butylene oxide or ethylene oxide/propylene oxide in a ratio of 0.1/9.9 to 9.9/0.1 or ethylene oxide/butylene oxide in a ratio of 0.1/9.9 to 9.9/0.1 in the molecule,
(3) alkyl or alkenyl sulfates having alkyl or alkenyl groups having 10 to 20 carbon atoms in average.
(4) olefinsulfonates having 10 to 20 carbon atoms in average in the molecule,
(5) alkanesulfonates having 10 to 20 carbon atoms in average in the molecule,
(6) saturated or unsaturated fatty acid salts having 10 to 24 carbon atoms in average in the molecule,
(7) alkyl or alkenyl ether carbonates having alkyl or alkenyl groups having 10 to 20 carbon atoms in average and also having 0.5 to 8 mol in average of added ethylene oxide, propylene oxide or butylene oxide or ethylene oxide/propylene oxide in a ratio of 0.1/9.9 to 9.9/0.1 or ethylene oxide/butylene oxide in a ratio of 0.1/9.9 to 9.9/0.1 in the molecule,
(8) α-sulfofatty acid salts or esters represented by the following formula:

$$R-\underset{SO_3Z}{\underset{|}{CH}}CO_2Y$$

wherein Y represents an alkyl group having 1 to 3 carbon atoms or a counter ion, Z represents a counter ion and R represents an alkyl or alkenyl group having 10 to 20 carbon atoms.

As the counter ions of the anionic surfactants, there may be mentioned alkali metal ions such as sodium and potassium ions; alkaline earth metal ions such as calcium and magnesium ions; ammonium ion; and alkanolamine ions having 1 to 3 alkanol groups having 2 or 3 carbon atoms, such as monoethanolamine, diethanolamine, triethanolamine and triisopropanolamine ions.

(9) amino acid-type surfactants represented by the following general formulae:

$$R_1-CO-N-CH-COOX \qquad \text{No. 1}$$
$$\phantom{R_1-CO-N-}|\phantom{CH}|$$
$$\phantom{R_1-CO-N-}R_2\phantom{CH}R_3$$

wherein $R_1$ represents an alkyl or alkenyl group having 8 to 24 carbon atoms, $R_2$ represents a hydrogen or an alkyl group having 1 or 2 carbon atoms, $R_3$ represents an amino acid residue and X represents an alkali metal or alkaline earth metal ion, $$R_1-CO-N-(CH_2)_n-COOX \qquad \text{No. 2}$$
$$\phantom{R_1-CO-N-}|$$
$$\phantom{R_1-CO-N-}R_2$$

wherein $R_1$, $R_2$ and X have the same meaning as above and n represents an integer of 1 to 5, $$\underset{R_1}{\overset{R_1}{\diagdown}}N-(CH_2)_m-COOX \qquad \text{No. 3}$$

wherein $R_1$ has the same meaning as above and m represents an integer of 1 to 8, $$R_1-N-CH-COOX \qquad \text{No. 4}$$
$$\phantom{R_1-}|\phantom{CH}|$$
$$\phantom{R_1-}R_4\phantom{CH}R_3$$

wherein $R_1$, $R_3$ and X have the same meaning as above and $R_4$ represents a hydrogen or an alkyl or hydroxyalkyl group having 1 or 2 carbon atoms, $$R_5-N-CH-COOX \qquad \text{No. 5}$$
$$\phantom{R_5-}|\phantom{CH}|$$
$$\phantom{R_5-}R_2\phantom{CH}R_3$$

wherein $R_2$, $R_3$ and X have the same meaning as above and $R_5$ represents a β-hydroxyalkyl or β-hydroxyalkenyl group having 6 to 28 carbon atoms, $$\underset{R_5}{\overset{R_5}{\diagdown}}N-CH-COOX \qquad \text{No. 6}$$
$$\phantom{XXXXX}|$$
$$\phantom{XXXXX}R_3$$

wherein $R_3$, $R_5$ and X have the same meaning as above,
(10) phosphate ester surfactants:

No. 1 alkyl (or alkenyl) hydrogenphosphates:

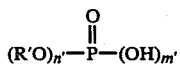

wherein R' represents an alkyl or alkenyl group having 8 to 24 carbon atoms, $n'+m'$ is 3 and $n'$ is 1 or 2, No. 2 alkyl (or alkenyl) phosphates:

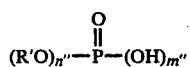

wherein R' has the same meaning as above, $n''+m''$ is 3 and $n''$ is 1 to 3,

No. 3 alkyl (or alkenyl) phosphate salts:

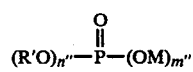

wherein R', $n''$ and $m''$ have the same meaning as above and M represents Na, K or Ca.

(11) sulfonic acid-type amphoteric surfactants of the following general formulae:

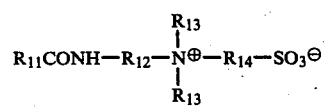
No. 1 wherein $R_{11}$ represents an alkyl or alkenyl group having 8 to 24 carbon atoms, $R_{12}$ represents an alkylene group having 1 to 4 carbon atoms, $R_{13}$ represents an alkyl group having 1 to 5 carbon atoms and $R_{14}$ represents an alkylene or hydroxyalkylene group.

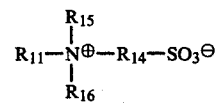
No. 2 wherein $R_{11}$ and $R_{14}$ have the same meaning as above and $R_{15}$ and $R_{16}$ represent an alkyl or alkenyl group having 8 to 24 carbon atoms or 1 to 5 carbon atoms,

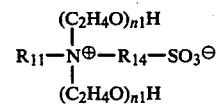
No. 3 wherein $R_{11}$ and $R_{14}$ have the same meaning as above and $n_1$ represents an integer of 1 to 20,

(12) betaine-type amphoteric surfactants represented by the following general formulae:

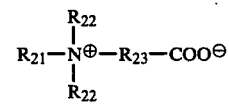
No. 1 wherein $R_{21}$ represents an alkyl, alkenyl, β-hydroxyalkyl or β-hydroxyalkenyl group having 8 to 24 carbon atoms, $R_{22}$ represents an alkyl group having 1 to 4 carbon atoms, and $R_{23}$ represents an alkylene or hydroxyalkylene group having 1 to 6 carbon atoms,

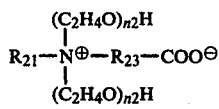
No. 2 wherein $R_{21}$ and $R_{23}$ have the same meaning as above and $n_2$ represents an integer of 1 to 20,

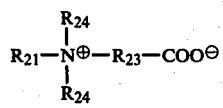
No. 3 wherein $R_{21}$ and $R_{23}$ have the same meaning as above and $R_{24}$ represents a carboxyalkyl or hydroxyalkyl group having 2 to 5 carbon atoms,

(13) polyoxyethylene alkyl or alkenyl ethers having an alkyl or alkenyl group having 10 to 20 carbon atoms in average and 1 to 20 mol of ethylene oxide added,

(14) polyoxyethylene alkylphenyl ethers having 6 to 12 carbon atoms in average and 1 to 20 mol of ethylene oxide added,

(15) polyoxypropylene alkyl or alkenyl ethers having an alkyl or alkenyl group having 10 to 20 carbon atoms in average and 1 to 20 mol of propylene oxide,

(16) polyoxybutylene alkyl or alkenyl ethers having an alkyl or alkenyl group having 10 to 20 carbon atoms in average and 1 to 20 mols of butylene oxide added,

(17) nonionic surfactants having an alkyl or alkenyl group having 10 to 20 carbon atoms in average and 1 to 30 mol in total of ethylene oxide/propylene oxide or ethylene oxide/butylene oxide (the ratio of ethylene oxide to propylene oxide or butylene oxide being 0.1/9.9 to 9.9/0.1),

(18) higher fatty acid alkanolamides of the following general formula or alkylene oxide adducts thereof:

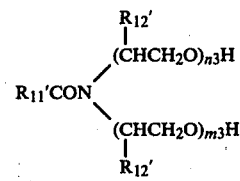

wherein $R_{11}'$ represents an alkyl or alkenyl group having 10 to 20 carbon atoms, $R_{12}'$ represents H or $CH_3$, $n_3$ represents an integer of 1 to 3 and $m_3$ represents an integer of 0 to 3,

(19) sucrose/fatty acid esters comprising fatty acids having 10 to 20 carbon atoms in average and sucrose,

(20) fatty acid/glycerol monoesters comprising fatty acids having 10 to 20 carbon atoms in average and glycerol,

(21) alkylamine oxides represented by the following general formula:

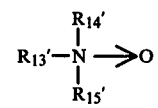

wherein $R_{13}'$ represents an alkyl or alkenyl group having 10 to 20 carbon atoms, and $R_{14}'$ and $R_{15}'$ represent an alkyl group having 1 to 3 carbon atoms,

(22) cationic surfactants represented by the following general formulae:

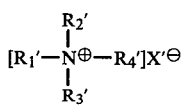 No. 1 wherein at least one of $R_1'$, $R_2'$, $R_3'$ and $R_4'$ represents an alkyl or alkenyl group having 8 to 24 carbon atoms and the other each represents an alkyl group having 1 to 5 carbon atoms, and $X'$ represents a halogen,

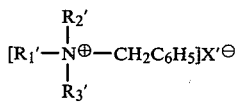 No. 2 wherein $R_1'$, $R_2'$, $R_3'$ and $R_4'$ have the same meaning as above,

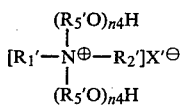 No. 3 wherein $R_1'$, $R_2'$ and $X'$ have the same meaning as above, $R_5'$ represents an alkylene group having 2 or 3 carbon atoms and $n_4$ represents an integer of 1 to 20.

At least one of the above-mentioned surfactants is incorporated in the composition preferably in an amount of at least 10 wt. %.

As preferred surfactants, there may be mentioned those of above items (1), (2), (3), (4), (5), (6), (11)-No. 2, (12)-No. 1, (13), (14), (15), (17) and (18).

[2] Sequestering agents for divalent metal ions:

0–50 wt. % of one or more builder components selected from the group of alkali metal salts and alkanolamine salts of the following compounds may be incorporated in the detergent composition:

(1) salts of phosphoric acids such as orthophosphoric acid, pyrophosphoric acid, tripolyphosphoric acid, metaphosphoric acid, hexametaphosphoric acid and phytic acid, (2) salts of phosphonic acids such as ethane-1,1-diphosphonic acid, ethane-1,1,2-triphosphonic acid, ethane-1-hydroxy-1,1-diphosphonic acid and derivatives thereof, ethanehydroxy-1,1,2-triphosphonic acid, ethane-1,2-dicarboxy-1,2-diphosphonic acid and methanehydroxyphosphonic acid, (3) salts of phosphonocarboxylic acids such as 2-phosphonobutane-1,2-dicarboxylic acid, 1-phosphonobutane-2,3,4-tricarboxylic acid and α-methylphosphonosuccinic acid, (4) salts of amino acids such as aspartic acid, glutamic acid and glycine, (5) salts of aminopolyacetic acids such as nitrilotriacetic acid, iminodiacetic acid, ethylenediaminetetraacetic acid, diethylenetriaminepentaacetic acid, glycol ether diaminetetraacetic acid, hydroxyethyliminodiacetic acid, triethylenetetraminehexaacetic acid and djenkolic acid, (6) high molecular weight electrolytes such as polyacrylic acid, polyaconitic acid, polyitaconic acid, polycitraconic acid, polyfumaric acid, polymaleic acid, polymesaconic acid, poly-α-hydroxyacrylic acid, polyvinylphosphonic acid, sulfonated polymaleic acid, maleic anhydride/diisobutylene copolymer, maleic anhydride/styrene copolymer, maleic anhydride/methyl vinyl ether copolymer, maleic anhydride/ethylene copolymer, maleic anhydride/ethylene crosslinked copolymer, maleic anhydride/vinyl acetate copolymer, maleic anhydride/acrylonitrile copolymer, maleic anhydride/acrylic ester copolymer, maleic anhydride/butadiene copolymer, maleic anhydride/isoprene copolymer, poly-β-ketocarboxylic acid derived from maleic anhydride and carbon monoxide, itaconic acid/ethylene copolymer, itaconic acid/aconitic acid copolymer, itaconic acid/maleic acid copolymer, itaconic acid/acrylic acid copolymer, malonic acid/methylene copolymer, mesaconic acid/fumaric acid copolymer, ethylene glycol/ethylene terephthalate copolymer, vinylpyrrolidone/vinyl acetate copolymer, 1-butene-2,3,4-tricarboxylic acid/itaconic acid/acrylic acid copolymer, polyester polyaldehyde carboxylic acid having quaternary ammonium group, cis-isomer of epoxysuccinic acid, poly[N,N-bis(carboxymethyl)acrylamide], poly(oxycarboxylic acid)s, starch/succinic, maleic or terephthalic acid ester, starch/phosphoric acid ester, dicarboxystarch, dicarboxymethylstarch and cellulose/succinic acid ester, (7) undissociative high molecular compounds such as polyethylene glycol, polyvinyl alcohol, polyvinylpyrrolidone and cold water-soluble, urethanized polyvinyl alcohol, (8) salts of organic acids such as dicarboxylic acids, e.g., oxalic acid, malonic acid, succinic acid, glutamic acid, adipic acid, pimelic acid, suberic acid, azelaic acid and decane-1,10-dicarboxylic acid; diglycolic acid, thiodiglycolic acid, oxalacetic acid, hydroxysuccinic acid, carboxymethyloxysuccinic acid and carboxymethyltartronic acid; hydroxydicarboxylic acids, e.g., glycolic acid, malic acid, hydroxypivalic acid, tartaric acid, citric acid, lactic acid, glyconic acid, mucic acid, glucuronic acid and dialdehydrostarch oxide; itaconic acid, methylsuccinic acid, 3-methylglutaric acid, 2,2-dimethylmalonic acid, maleic acid, fumaric acid, glutamic acid, 1,2,3-propanetricarboxylic acid, aconitic acid, 3-butene-1,2,3-tricarboxylic acid, butane-1,2,3,4-tetracarboxylic acid, ethanetetracarboxylic acid, ethenetetracarboxylic acid, n-alkenylaconitic acids, 1,2,3,4-cyclopentanetetracarboxylic acid, phthalic acid, trimesic acid, hemimellitic acid, pyromellitic acid, benzenehexacarboxylic acid, tetrahydrofuran-1,2,3,4-tetracarboxylic acid and tetrahydrofuran-2,2,5,5-tetracarboxylic acid; sulfonated carboxylic acids, e.g., sulfoitaconic acid, sulfotricarballylic acid, cysteic acid, sulfoacetic acid and sulfosuccinic acid; carboxymethylated sucrose, lactose or raffinose, carboxymethylated pentaerythritol, carboxymethylated gluconic acid, condensates of polyhydric alcohols or sugars with maleic anhydride or succinic anhydride, condensates of hydroxycarboxylic acids with maleic anhydride or succinic anhydride, CMOS and builder M, (9) aluminosilicates:

No. 1 crystalline aluminosilicates represented by the following formula:

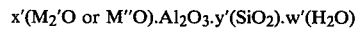

wherein M' represents an alkali metal atom, M'' represents an alkaline earth metal atom exchangeable with calcium, and x', y' and w' represent mol numbers of the respective components and generally, $0.7 \leq x' \leq 1.5$, $0.8 \leq y' \leq 6$ and w' represents a positive integer, No. 2 As builders for the detergents, compounds represented by the following general formula are particularly preferred:

$$Na_2O \cdot Al_2O_3 \cdot nSiO_2 \cdot wH_2O$$

wherein n represents a number of 1.8 to 3.0 and w represents a number of 1 to 6, No. 3 amorphous aluminosilicates represented by the following formula:

$$x(M_2O) \cdot Al_2O_3 \cdot y(SiO_2) \cdot w(H_2O)$$

wherein M represents sodium and/or potassium atom and x, y and w represent mol numbers of the respective components within the following ranges:

$$0.7 \leqq x \leqq 1.2$$

$$1.6 \leqq y \leqq 2.8$$

w represents a positive integer including 0, No. 4 amorphous aluminosilicates represented by the following formula:

$$X(M_2O) \cdot Al_2O_3 \cdot Y(SiO_2) \cdot Z(P_2O_5) \cdot \omega(H_2O)$$

wherein M represents Na or K, and X, Y, Z and ω represent mol numbers of the respective components within the following ranges:

$$0.20 \leqq X \leqq 1.10$$

$$0.20 \leqq Y \leqq 4.00$$

$$0.001 \leqq Z \leqq 0.80$$

ω: a positive integer including 0,

[3] Alkalis and inorganic electrolytes:

1–50 wt.%, preferably 5–30 wt.%, of one or more alkali metal salts of the following compounds may be incorporated in the detergent composition as alkalis or inorganic electrolytes: salts of silicic acid, carbonic acid and sulfuric acid; and organic alkalis such as triethanolamine, diethanolamine, monoethanolamine and triisopropanolamine,

[4] Antiredeposition agents:

0.1–5% of one or more compounds selected from the following group may be incorporated in the composition as antiredeposition agents: polyethylene glycol, polyvinyl alcohol, polyvinylpyrrolidone and crboxymethylcellulose.

Particularly, a combination of carboxymethylcellulose or/and polyethylene glycol with the alkali cellulase of the present invention exhibits a synergism in the removal of muddy dirts.

To avoid the decomposition of carboxymethylcellulose by the alkali cellulase in the detergent, it is desirable that carboxymethylcellulose to be incorporated in the composition is granulated or coated.

[5] Bleaching agents:

A combination of the alkali cellulase of the present invention with a bleaching agent such as sodium percarbonate, sodium perborate, sodium sulfate/hydrogen peroxide adduct or sodium chloride/hydrogen peroxide adduct and/or zinc salt of sulfonated phthalocyanine or a photosensitive bleaching colorant such as an aluminum salt further improves the deterging effects.

[6] Enzymes (those exhibiting their essential enzymatic effects in the deterging step):

From the reactivity, these enzymes may be classified into the groups of hydrolases, lyases, oxidoreductases, ligases, transferases and isomerases. Any of them may be used in the present invention. Particularly preferred are hydrolases including proteases, esterases, carbohydrases and nucleases.

As examples of the proteases, there may be mentioned pepsin, trypsin, chymotrypsin, collagenase, keratinase, elastase, subtilisin, BPN, papain, bromelin, carboxypeptidases A and B, aminopeptidase and aspergillopeptidases A and B.

As examples of esterases, there may be mentioned gastric lipase, pancreatic lipase, vegetable lipases, phospholipases, choline esterases and phosphatases.

As carbohydrases other than the specified cellulases which characterize the present invention, there may be mentioned those used generally in the prior art such as cellulase, maltase, saccharase, amylase, pectinase, lysozyme, α-glucosidase and β-glucosidase.

[7] Blueing agents and fluorescent dyes:

Various blueing agents and fluorescent dyes may also be incorporated in the composition. Those having the following structures are recommended:

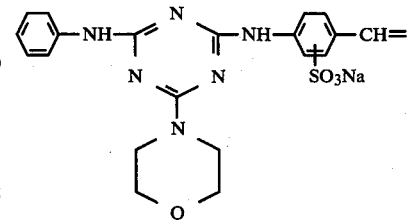

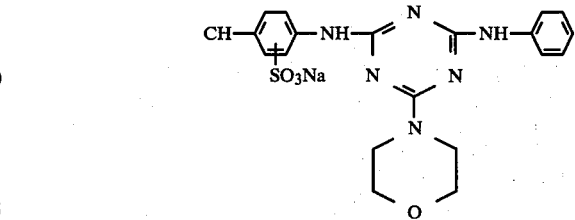

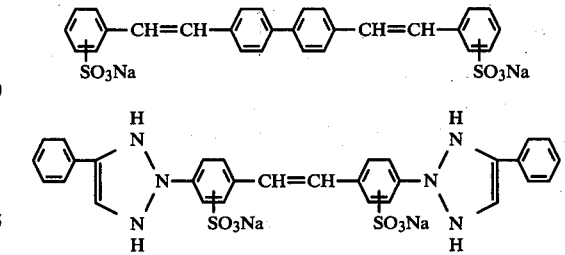

Blueing agents represented by the following general formulae:

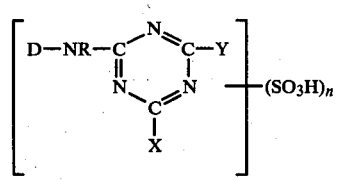

wherein D represents a residue of blue or purple monoazo, disazo or anthraquinone dyestuff, X and Y represent a hydroxyl group, amino group, aliphatic amino group which may be substituted with hydroxyl, sulfonic acid, carboxylic acid or alkoxyl group, or aromatic amino or cycloaliphatic amino group which may be substituted with a halogen atom, hydroxyl, sulfonic acid, carboxylic acid, lower alkyl, or lower alkoxyl group, R represents a hydrogen atom or lower alkyl group, with the proviso that the case when R represents a hydrogen atom and (1) both X and Y represent hydroxyl or alkanolamino groups at the same time, or (2) one of X and Y represents a hydroxyl group and the other represents an alkanolamino group is excluded, and n represents an integer of at least 2,

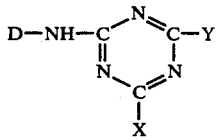

wherein D represents a residue of blue or purple azo or anthraquinone dyestuff, and X and Y represent the same or different alkanolamine residue or hydroxyl group,

[8] Caking inhibitors:

The following caking inhibitors may be incorporated in the powdery detertent: p-toluenesulfonates, xylenesulfonates, acetates, sulfosuccinates, talc, finely pulverized silica, clay, calcium silicate (such as Micro-cell; a product of Johns-Manvill Co.), calcium carbonate and magnesium oxide,

[9] Masking agents for cellulase activity-inhibiting factors:

In some cases, the cellulase is deactivated in the presence of ions and compounds of copper, zinc, chromium, mercury, lead, manganese and silver. To mask these inhibiting factors, various metal chelating agents and metal precipitating agents are effective. They include the sequestering agents for divalent metal ions listed in above item [2] or/and magnesium silicate and magnesium sulfate.

In some cases, cellobiose, glucose and gluconolactone serve as the inhibiting factors. Therefore, the coexistence of these sugars with the cellulase should be avoided as far as possible. When the coexistence is unavoidable, a direct contact of the sugar with the cellulase should be avoided by, for example, coating the respective components.

Powerful chelating agents such as ethylenediaminetetraacetates, anionic surfactants and cationic surfactants serve as the inhibiting factors in some cases. However, the coesistence of these substances with the cellulase is also possible when they are shaped into tablets or coated.

The above-mentioned masking agents or the methods can be employed, if necessary.

[10] Cellulase-activators:

When protein, cobalt or its salts, calcium or its salts, potassium or its salts, sodium or its salts or monosaccharides such as mannose or xylose are incorporated in the composition, the cellulase is activated and the deterging effects are improved remarkably, though the effects are somewhat different depending on the kind of cellulase.

[11] Antioxidants:

The antioxidants include, for example, tertbutylhydroxytoluene, 4,4'-butylidenebis-(6-tert-butyl-3-methylphenol), 2,2'-butylidenebis-(6-tert-butyl-4-methylphenol), monostyrenated cresol, distyrenated cresol, monostyrenated phenol, distyrenated phenol and 1,1'-bis-(4-hydroxyphenyl)cyclohexane.

[12] Solubilizers:

The solubilizers include, for example, lower alcohols such as ethanol, benzenesulfonic acid salts, lower alkylbenzenesulfonates such as p-toluenesulfonate, glycols such as propylene glycol, acetylbenzenesulfonates, acetamides, pyridinedicarboxylic acid amides, benzoates and urea.

Thus, according to the present invention, excellent deterging effects can be obtained over a wide pH range of the deterging bath by using the detergent composition of the present invention containing the specified cellulase produced by alkalophilic bacteria of the genus of Cellulomonas which cellulase exhibits a high activity under alkaline conditions and has a high alkali resistance.

As for the builder effects exhibited as the pH of the deterging bath is reduced in the course of the deterging step, the effects more than make up for the reduction in the deterging power due to alkalinity reduction.

The enzymatic activity of the cellulase is determined as follows in the present invention:

50 mg of Avicel (for chromatography) or carboxymethylcellulose (CMC) is suspended in 4 ml of glycine NaCl-NaOH buffer solution (pH 8.3). The suspension is preheated at 37° C. for 5 min. 1 ml of an enzyme solution is added to the suspension and the mixture is stirred thoroughly and then left to react for 1 h. After completion of the reaction, the reducing sugar is determined by the 3,5-dinitrosalicylic acid method. More particularly, the reaction liquid is filtered and 3 ml of 3,5-dinitrosalicylic acid reagent is added to 1 ml of the filtrate. The mixture is heated to 100° C. for 10 min to develop a color. After cooling, ion-exchanged water is added thereto to control the total volume to 25 ml. The resulting sample is subjected to colorimetry at a wave length of 500 m$\mu$.

As for the enzyme activity unit, 1 unit/mg-solid indicates that 1 mg of solid enzyme forms a reducing sugar in an amount corresponding to 1 $\mu$mol of glucose per hour.

As for the specified cellulase content of the detergent composition of the present invention, the composition contains preferably 0.01 to 70 wt%, particularly 0.1 to 10 wt.%, of cellulase having an enzymatic activity of at least 0.001 unit/mg-solid. In other words, the cellulase content is such that the cellulase in the bath shows an enzymatic activity of preferably 0.1 to 1000 units/l, particularly 1 to 100 units/l.

The following examples will further illustrate the present invention in more detail. In referential examples, the production of cellulase is described. Unless otherwise state, percentages are given by weight.

Referential Example 1

Cellulomonas sp. No. 301-A (FERM-P 6582) was inoculated in a medium comprising 1.0% of Avicel, 0.2% of yeast extract, 0.2% of sodium nitrate, 0.1% of dipotassium hydrogenphosphate, 0.05% of magnesium sulfate heptahydrate, 1.0% of sodium hydrogencarbonate and the balance of water. Shaking culture was effected at 30° C.

After effecting the culture for 5 days, the microbes were removed by centrifugation. The resulting culture liquid was fractionated using ammonium sulfate. The resulting solid was freeze-dried to obtain an enzyme powder. 0.5 g of the enzyme powder was obtained per liter of the culture liquid.

The resulting enzyme had CMC-destruction activities of 1.02 mg/mg.min. and 0.82 mg/mg.min. (in term of glucose) at pH 7.0 and 9.0, respectively and Avicel-destruction activities of 0.051 mg/mg.min. and 0.041 mg/mg.min. (in terms of glucose) at pH 7.0 and 9.0, respectively.

Referential Example 2

An enzyme powder was obtained from a culture liquid obtained in the same manner as in Referential Example 1 except that 1.0% of Avicel used as a carbon source in Referential Example 1 was replaced with 1.0% of CMC. The resulting enzyme had CMC-destruction activities of 0.41 mg/mg.min. and 0.36 mg/mg.min. (in terms of glucose) at pH 7.0 and 9.0, respectively.

The CMC-destruction activity and Avicel-destruction activity were determined as follows:

0.1 ml of the enzyme solution was added to 0.2 ml of 2.5% CMC, sodium salt of A01MC, tradename of a product of San'yo Kokusaku Pulp Co.), 0.1 ml of 0.5 M glycine-NaOH buffer solution (pH 9) (0.5 M phosphate buffer solution when the determination was effected at pH 7) and 0.1 ml of deionized water and the reaction was carried out at 50° C. for 20 min.

After completion of the reaction, the resulting reducing sugar was determined with 3,5-dinitrosalicylic acid reagent (DNS reagent) and the results were represented after conversion into glucose. 1.0 ml of DNS reagent was added to 0.5 ml of the reaction liquid. The mixture was heated in boiling water for 5 min to develop a color. After cooling, the mixture was diluted with 4.5 ml of deionized water. The colorimetric determination was effected at a wave length of 535 nm to determine an exo-type CMC-destruction enzymatic activity.

The Avicel-destruction enzymatic activity was determined by carrying out the reaction for several hours in the same manner as above except that the total amount of the reaction system was 5 ml and that CMC was replaced with 50 mg of Avicel and then subjecting the resulting reducing sugar to the colorimetric determination in the same manner as above.

As for enzymatic activity units of the enzymes obtained in the above Referential Examples 1 and 2, they were 130 units/mg.solid and 52 units/mg.solid as determined by the above-mentioned enzymatic activity-measuring method.

In examples given below, the following experimental conditions were employed:

(1) Naturally stained collars:

A piece of cotton shirting #2023 was sewed on a collar of each shirt. After worn by male adults for 3 days, the shirts were kept at 25° C. and at 65% RH for one month. Thereafter, the shirts were divided into 3 groups according to the degree of stain. Cloths having a center of symmetrical stain distribution were selected from the group of the highest degree of stain. The cloths were cut into halves at the center of symmetry to obtain test samples.

(2) Deterging conditions and method:

In deterging the naturally stained cloths, the cloths having a size of 9 cm×30 cm were divided into halves at the center of symmetry. One of the halves of the stained cloths having a size of 9 cm×15 cm was washed using an enzyme-free detergent (standard detergent) and the other was washed using the detergent of the present invention (comparative detergent). The experiment was effected as follows: 15 sheets of the naturally stained clothes were sewed on cotton cloths having a size of 50 cm×50 cm. When a powdery detergent was used, 1 kg in total of the stained cloth and cotton underwears were placed in 6 l of 0.665% detergent solution. After immersion at 30° C. for 2 h, the whole was transferred into a washing machine (Ginga; a product of Toshiba Co., Ltd.). Water was added thereto to make the total quantity 30 l. The washing was effected according to a strong reverse turn stream system for 10 min. After drying, the results were judged. When a liquid detergent was used, 20 cc of the liquid detergent was applied uniformly to the stained cloths. After leaving them to stand for 10 min, 1 kg in total of these cloths and underwears were placed in the washing machine (Ginga; a product of Toshiba Co., Ltd.). Water was added thereto to make the total quantity 30 l. The washing was effected according to a strong reverse turn stream system for 10 min. After drying, the results were judged.

Each pair of the halves washed with the standard detergent and the detergent of the present invention was compared with each other with the naked eye. The degrees of stain were represented on the basis of 10 standard ranks. The deterging power of the detergent of the present invention was represented by a point as compared with the deterging power of the standard detergent represented by 100. A difference in the deterging power index of at least 0.5 may be considered to be significant.

(3) Enzymes used:
(1) Cellulase of the present invention (cellulase obtained in Referential Example 1, which was further diluted with Glauber's salt into 1/20 concentration and granulated),
(2) Cellulase of the present invention (cellulase obtained in Referential Example 2, which was further diluted with Glauber's salt into 1/20 concentration and granulated),
(3) Cellulase (Type I of SIGMA Co.; produced by Aspergillus niger),
(4) Lipase (a product of Gist Brocades N.V.; produced by R. oryzae),
(5) Amylase (Termamyl 60 G; a product of NOVO Industries Co.),
(6) Protease (Alkalase 2.0 M; a product of NOVO Industries Co.).

Example 1

Highly alkaline, powdery detergents for clothes having the following composition were prepared. A 0.665% aqueous solution of the detergent had a pH of 11.3.

| | |
|---|---|
| sodium n-dodecylbenzenesulfonate | 20 wt. % |
| soap (sodium salts of tallow fatty acids) | 2 |
| sodium orthophosphate | 20 |
| sodium metasilicate | 10 |
| sodium carbonate | 15 |
| carboxymethylcellulose | 1 |
| polyethylene glycol | 1 |
| fluorescent dye | 0.4 |
| Glauber's salt | balance |
| enzyme | 0 or 2 |
| water | 5 |

The results of the deterging tests of the resulting detergents are shown in Table 1. In the table, the detergents are represented by (example No.)-(No. of enzyme used). [When no enzyme was used, the detergent is represented by (example No.)- ⓪]

TABLE 1

| Detergent No. | | Deterging power index |
|---|---|---|
| 1-⓪ | (Standard detergent) | 100 |
| 1-① | (Present invention) | 102 |
| 1-② | (Present invention) | 101.5 |
| 1-③ | | 100.5 |
| 1-④ | | 100 |
| 1-⑤ | | 100 |
| 1-⑥ | | 100.5 |

Example 2

Weakly alkaline, powdery detergents for clothes having the following composition were prepared. A pH of a 0.665% aqueous solution of the detergent was 10.5.

| | |
|---|---|
| sodium α-olefinsulfonate | 10 wt. % |
| sodium n-dodecylbenzenesulfonate | 10 |
| soap | 1 |
| sodium tripolyphosphate | 20 |
| sodium silicate | 10 |
| (JIS No. 2 sodium silicate) | |
| sodium carbonate | 5 |
| carboxymethylcellulose | 1 |
| polyethylene glycol | 1 |
| fluorescent dye | 0.4 |
| Glauber's salt | balance |
| enzyme | 0 or 2 |
| water | 10 |

The results of the deterging tests carried out in the same manner as in Example 1 are shown in Table 2.

TABLE 2

| Detergent No. | | Deterging power index |
|---|---|---|
| 2-⓪ | (Standard detergent) | 100 |
| 2-① | (Present invention) | 103 |
| 2-② | (Present invention) | 102 |
| 2-④ | | 100 |
| 2-⑤ | | 100 |
| 2-⑥ | | 100.5 |

Example 3

Neutral, powdery detergents for clothes having the following composition were prepared. A pH of a 0.665% aqueous solution of the detergent was 7.2.

| | |
|---|---|
| sodium straight-chain alcohol (C = 14) sulfate | 30 wt. % |
| polyethylene glycol | 1 |
| sodium phosphate | 1 |
| fluorescent dye | 0.2 |
| Glauber's salt | balance |
| enzyme | 0 or 2 |
| water | 5 |

The results of the deterging tests of the detergents are shown in Table 3.

TABLE 3

| Detergent No. | | Deterging power index |
|---|---|---|
| 3-⓪ | (Standard detergent) | 100 |
| 3-① | (Present invention) | 103 |
| 3-② | (Present invention) | 102 |
| 3-④ | | 100 |
| 3-⑤ | | 100 |
| 3-⑥ | | 100 |

Example 4

Phosphorus-free, weakly alkaline detergents having the following composition were prepared:

| | |
|---|---|
| sodium n-dodecylbenzenesulfonate | 15 wt. % |
| sodium alkylethoxysulfate | 5 |
| ($C_{14}$–$C_{15}$, $\overline{EO}$ = 3 mol) | |
| builder and enzyme (see Table 4) | 20 |
| sodium silicate | 15 |
| sodium carbonate | 15 |
| sodium polyacrylate | 1.5 |
| polyethylene glycol | 1.5 |
| fluorescent dye | 0.5 |
| Glauber's salt | balance |
| water | 5 |

The results of the deterging test are shown in Table 4.

TABLE 4

| Builder | Enzyme | Deterging power index |
|---|---|---|
| sodium tripolyphosphate 20% | — | 100 (Standard detergent) |
| sodium citrate 20% | — | 98 |
| 4A zeolite 20% | — | 98.5 |
| sodium citrate 15% | ⑥5% | 98.5 |
| 4A zeolite 15% | ⑥5% | 98.5 |
| sodium citrate 15% | ①5% | 102 (Present invention) |
| sodium citrate 15% | ②5% | 101.5 (Present invention) |
| 4A zeolite 15% | ①5% | 101.5 (Present invention) |
| 4A zeolite 15% | ②5% | 101 (Present invention) |

Example 5

Detergents having the same composition as in Example 2 but containing various combinations of enzymes were prepared. The results of the deterging test of the resulting detergents are shown in Table 5.

TABLE 5

| Detergent No. | | Combination of enzymes Numerals on the right side represent percentages of each enzyme | Deterging power index |
|---|---|---|---|
| 2-① | (Standard detergent) | ① = 2 | 100 |
| 2-① /④ | (Present invention) | ① /④ = 1/1 | 101 |
| 2-① /⑤ | (Present invention) | ① /⑤ = 1/1 | 101 |
| 2-① /⑥ | (Present invention) | ① /⑥ = 1/1 | 101.5 |
| 2-① /④ /⑥ | (Present invention) | ① /④ /⑥ = 1/0.5/0.5 | 101.5 |
| 2-① /⑤ /⑥ | (Present invention) | ① /⑤ /⑥ = 1/0.5/0.5 | 102 |
| 2-④ /⑤ /⑥ | | ④ /⑤ /⑥ = 1/0.5/0.5 | 98 |

Example 6

Weakly alkaline, powdery detergents for clothes having the following composition were prepared:

| | |
|---|---|
| sodium alkylsulfate ($\overline{C} = 14.5$) | 15% |
| sodium alkylethoxysulfate | 5 |
| ($\overline{C} = 14.5$, $\overline{EO} = 3$) | |
| soap (tallow fatty acid soap) | 2 |
| sodium pyrophosphate | 18 |
| sodium silicate | 13 |
| sodium carbonate | 5 |
| polyethylene glycol | 2 |
| fluorescent dye | 0.2 |
| Galuber's salt | balance |
| magnesium silicate | 1 |
| water | 5 |
| enzyme | 2 |
| sodium percarbonate | 15 |

The results of the deterging test of the resulting detergents are shown in Table 6.

TABLE 6

| Detergent No. | | Enzyme | Deterging power index |
|---|---|---|---|
| 6-⑥ | (Standard detergent) | ⑥ | 100 |
| 6-① | (Present invention) | ① | 102.5 |
| 6-② | (Present invention) | ② | 101.5 |

Example 7

Weakly alkaline, liquid detergents for clothes having the following composition were prepared. A pH of a stock solution of the detergents was 9.5.

| | |
|---|---|
| sec-alcohol ethoxylate ($\overline{C} = 13.5$, $\overline{EO} = 7.0$) | 10% |
| sodium n-dodecylbenzenesulfonate | 20 |
| coconut fatty acid diethanolamide | 3 |
| carboxymethylcellulose | 1 |
| polyethylene glycol ($\overline{MW}$ 6000) | 2 |
| potassium pyrophosphate | 14 |
| sodium formate | 1 |
| calcium chloride | 0.01 |
| sodium m-xylenesulfonate | 5 |
| enzyme | 2 |
| water | balance |
| total | 100% |

The results of the deterging test of the resulting detergents are shown in Table 7.

TABLE 7

| Detergent No. | | Deterging power index |
|---|---|---|
| 7-⑥ | (Standard detergent) | 100 |
| 7-① | (Present invention) | 103 |
| 7-② | (Present invention) | 102.5 |
| 7-⑤ | | 97 |

Example 8

Neutral, liquid detergents for clothese having the following composition were prepared. A pH of a stock solution of the detergent was 7.0.

| | |
|---|---|
| sodium alkylethoxysulfate | 20% |
| ($C_{14-15}$, $\overline{EO} = 3.0$ mol) | |
| sec-alcohol ($\overline{C} = 13.5$) ethoxylate ($\overline{EO} = 7$) | 25 |
| triethanolamine | 1 |
| polyethylene glycol ($\overline{MW}$ 6000) | 2 |
| carboxymethylcellulose | 1 |
| citric acid | 1 |
| fluorescent dye | 0.3 |
| blueing agent | 0.05 |
| EtOH | 8 |
| water | balance |
| enzyme | 2 |
| total | 100% |

The results of the deterging test of the resulting detergents are shown in Table 8.

TABLE 8

| Detergent No. | | Deterging power index |
|---|---|---|
| 8-④ | (Standard detergent) | 100 |
| 8-① | (Present invention) | 103 |
| 8-② | (Present invention) | 102 |
| 8-⑥ | | 100 |

The embodiments of the invention in which an exclusive property or privilege is claimed are defined as follows:

1. A detergent composition which comprises 0.01 to 70 percent by weight of a cellulase produced by alkalophilic bacteria of the genus of Cellulosmonas and the balance of cleaning agents.

2. A detergent composition as claimed in claim 1, in which the strain of alkalophilic bacteria of the genus of Cellulomonas is Cellulomonas sp. No. 301-A, deposited as FERM-P 6582.

* * * * *

UNITED STATES PATENT AND TRADEMARK OFFICE
CERTIFICATE OF CORRECTION

PATENT NO. : 4 443 355
DATED : April 17, 1984
INVENTOR(S) : Murata et al

It is certified that error appears in the above-identified patent and that said Letters Patent is hereby corrected as shown below:

Column 18, line 44, please change "Cellulosmonas" to
---Cellulomonas---.

Signed and Sealed this

Fourth Day of December 1984

[SEAL]

Attest:

GERALD J. MOSSINGHOFF

Attesting Officer  Commissioner of Patents and Trademarks